US011739384B2

(12) United States Patent
Moller et al.

(10) Patent No.: US 11,739,384 B2
(45) Date of Patent: Aug. 29, 2023

(54) CIRCULATING SERUM MICRORNA BIOMARKERS AND METHODS FOR PARKINSON'S DISEASE PROGNOSIS

(71) Applicant: ST. JOHN'S UNIVERSITY, Queens, NY (US)

(72) Inventors: Simon Geir Moller, Queens, NY (US); Indranil Basak, Queens, NY (US); Ketan Patil, Queens, NY (US); Jan Petter Larsen, Queens, NY (US); Guido Werner Alves, Queens, NY (US)

(73) Assignee: ST. JOHN'S UNIVERSITY, Queens, NY (US)

( * ) Notice: Subject to any disclaimer, the term of this patent is extended or adjusted under 35 U.S.C. 154(b) by 326 days.

(21) Appl. No.: 16/623,870

(22) PCT Filed: Jun. 7, 2018

(86) PCT No.: PCT/US2018/036380
§ 371 (c)(1),
(2) Date: Dec. 18, 2019

(87) PCT Pub. No.: WO2018/236590
PCT Pub. Date: Dec. 27, 2018

(65) Prior Publication Data
US 2021/0198737 A1    Jul. 1, 2021

Related U.S. Application Data

(60) Provisional application No. 62/521,797, filed on Jun. 19, 2017.

(51) Int. Cl.
*C12Q 1/6883* (2018.01)

(52) U.S. Cl.
CPC ...... *C12Q 1/6883* (2013.01); *C12Q 2600/112* (2013.01); *C12Q 2600/158* (2013.01); *C12Q 2600/178* (2013.01)

(58) Field of Classification Search
CPC .............................................. C12Q 2600/112
See application file for complete search history.

(56) References Cited

U.S. PATENT DOCUMENTS

| 2014/0235697 | A1 | 8/2014 | Weiner et al. |
| 2014/0322354 | A1* | 10/2014 | Goel ........................ A61B 1/31 435/6.12 |
| 2015/0197809 | A1 | 7/2015 | Myers et al. |

FOREIGN PATENT DOCUMENTS

| WO | 2014/018650 | 1/2014 |
| WO | 2014/075822 | 5/2014 |
| WO | 2015/073972 | 5/2015 |
| WO | 2015/091892 | 6/2015 |

OTHER PUBLICATIONS

Hoss et al. Front Ageing Neurosci. 2016. 8:36. (Year: 2016).*
Table S2 from Hoss et al. Front Ageing Neurosci. 2016. 8:36. (Year: 2016).*
Burgos et al. PLOS ONE. 2014. 9(5):e94839. (Year: 2014).*
Takousis et al. Alzheimer's & Dementia. 2019. pp. 1-10. (Year: 2019).*
Martinez et al. Neural Regen Res. 2020. 15(4):606-619. (Year: 2020).*
Hicks et al. Journal of Neurotrauma. 2018. 35:64-72. (Year: 2018).*
Weber et al. Clin Chem. 2010. 56(11): 1733-1741. (Year: 2010).*
Raoof et al. Scientific Reports. 2017. 7:3328. (Year: 2017).*
Hasan et al., "A Computational Approach for Predicting Role of Human MicroRNAs in MERS-CoV Genome", Advances in Bioinformatics, vol. 2014, Article ID 967946 (2014) 1-8.
Hoss, "The relationship of microRNAs to clinical features of Huntington's and Parkinson's disease", Boston University (2016) XP055509224.
Khoo, "Circulating microRNAs as Progression Biomarkers for Parkinson's Disease", Fox Foundation (2014) XP055497097.
Khoo, "Circulating MicroRNAs: a New Paradigm for Parkinson's Disease Biomarker Discovery", Fox Foundation (2014) XP055497095.
Shu et al., "APP intracellular domain acts as a transcriptional regulator of miR-663 suppressing neuronal differentiational", Cell Death and Disease, vol. 6, No. 2 (2015) 1-12.
Patil, Ketan Shirish, Biomarkers and Target Discovery in Parkinson's Disease, Dissertation of Biological Sciences St. John's College of Liberal Arts and Sciences at St. John's University New York, ProQuest, Copyright 2016.
Aarsland, et al. The Epidemiology of Dementia Associated with Parkinson Disease, Journal of the Neurological Sciences 289 (2010) 18-22.
Genetic and Rare Diseases Information Center, "Rapid-Onset Dystonia-Parkinsonism," pp. 1-9.
Hely, et al. The Sydney Multicenter Study of Parkinson's Disease: The Inevitability of Dementia at 20 years, Movement Disorders, vol. 23, No. 6, 2008, pp. 837-844.
Tsiouris et al., Predicting Rapid Progression of Parkinson's Disease at Baseline Patients Evaluation, IEEE, 2017 pp. 3898-3901.
Tsiouris et al., Prognostic Factors of Rapid Symptoms Progression in Patients with Newly Diagnosed Parkinson's Disease, Artificial Intelligence in Medicine 103 (2020), pp. 1-15.
Brashear, et al., ATP1A3-Related Neurologic Disorders, U.S. National Library of Medicine, GeneReviews, University of Washington (2008) 1-27.
Rosewich, et al., Research Conference Summary from the 2014 International Task Force on ATP1A3-Related Disorders, American Academy of Neurology (2017) 1-7.

* cited by examiner

*Primary Examiner* — Joseph G. Dauner
(74) *Attorney, Agent, or Firm* — Venable LLP (57) ABSTRACT

Biomarkers and methods for identifying, verifying and confirming circulating serum-based microRNAs. The microRNAs (PrognomiRs) can be used to differentiate patient's suffering from rapid progressing Parkinson's disease (PD) from slow progressing PD patients.

19 Claims, 1 Drawing Sheet
Specification includes a Sequence Listing.

CIRCULATING SERUM MICRORNA BIOMARKERS AND METHODS FOR PARKINSON'S DISEASE PROGNOSIS

This application is a national phase of PCT Application No. PCT/US2018/036380 filed Jun. 7, 2018, which in turn claims benefit of U.S. Provisional Patent Application No. 62/521,797 filed Jun. 19, 2017, which are hereby incorporated by reference herein in their entirety.

BACKGROUND OF THE INVENTION

1. Field of the Invention

The present invention generally relates to serum-based microRNAs and methods for differentiating patients suffering from Parkinson's disease based on the rate of disease progression, as well as assisting clinicians to determine treatment protocols for such patients.

2. Brief Description of the Background Art

Parkinson's Disease (PD) is a highly specific degeneration of dopamine-containing cells of the substantia nigra of the midbrain, causing a dopamine deficiency in the striatum. PD currently affects about 10 million people world-wide. Effective management of a patient with PD is possible in the first 5-7 years of treatment, after which time a series of often debilitating complications, together referred to as Late Motor Fluctuations (LMF) occur. It is believed that treatment with levodopa ((−)-L-α-amino-beta-(3,4-dihydroxybenzene) propanoic acid), or L-dopa, the most effective antiparkinson drug, may facilitate or even promote the appearance of LMF. Dopamine agonists are employed as a treatment alternative, but they do not offer the same degree of symptomatic relief to patients as L-dopa does.

Symptomatic therapies improve signs and symptoms without affecting the underlying disease state. Levodopa increases dopamine concentration in the striatum, especially when its peripheral metabolism is inhibited by a peripheral decarboxylase inhibitor (PDI). Levodopa/PDI therapy is widely used for symptomatic therapy for Parkinson's disease, such as combinations with levodopa, with carbidopa ((−)-L-α-hydrazino-α-methyl-beta-(3,4-dihydroxybenzene) propanoic acid monohydrate), levodopa and controlled release carbidopa, levodopa and benserazide, levodopa plus controlled release benserazide (2-Amino-3-hydroxy-propionic acid N'-(2,3,4-trihydroxy-benzyl)-hydrazide).

Catechol-O-methyltransferase (COMT) inhibitors enhance levodopa treatment as they inhibit levodopa's metabolism, enhancing its bioavailability and thereby making more of the drug available in the synaptic cleft for a longer period of time. Examples of COMT inhibitors include tolcapone (3,4-dihydroxy-4'-methyl-5-nitrobenzophenone) and entacapone ((E)-2-cyano-3-(3,4-dihydroxy-5-nitrophenyl)-N,N-diethyl-2-propenamide).

Dopamine agonists provide symptomatic benefit by directly stimulating post-synaptic striatal dopamine receptors. Examples include bromocriptine ((5a)-2-Bromo-12'-hydroxy-2'-(1-methylethyl)-5'-(2-methylpropyl)erg-otaman-3',6',18-trione), pergolide (8B-[(Methylthio)methyl]-6-propylergoline), ropinirole (4-[2-(Dipropylamino)ethyl]-1,3-dihydro-2H-indol-2-one), pramipexole ((S)-4,5,6,7-Tetrahydro-$N^6$-propyl-2,6-benzothiazolediamine), lisuride (N'-[(8α)-9,10-didehydro-6-methylergolin-8-yl]-N,N-diethyl-urea), cabergoline ((8β)-N-[3-(Dimethylamino)propyl]-N-[(ethylamino)carbonyl]-6-(2-propenyl)ergoline-8-carboxamide), apomorphine ((6aR)-5,6,6a,7-Tetrahydro-6-methyl-4H-dibenzo[de,g]quinoline-10,11-diol), sumanirole (5-(methylamino)-5,6-dihydro-4H-imidazo {4,5,1-ij}quinolin-2(1H)-one), rotigotine ((−)(S)-5,6,7,8-tetrahydro-6-[propyl[2-(2-thienyl)ethyl]amino]-1-naphthol-), talipexole (5,6,7,8-Tetrahydro-6-(2-propenyl)-4H-thiazolo[4,5-d]azepin-2-amine), and dihydroergocriptine (ergotaman-3',6',18-trione,9,10-dihydro-12'-hydroxy-2'-methyl-5'-(phenylmethyl) (5' cc)). Dopamine agonists are effective as monotherapy early in the course of Parkinson's disease and as an adjunct to levodopa in more advanced stages. Unlike levodopa, dopamine agonists directly stimulate post-synaptic dopamine receptors. They do not undergo oxidative metabolism and are not thought to accelerate the disease process.

Amantidine (1-Aminotricyclo $(3,3,1,1^{3,7})$ decane) is an antiviral agent that was discovered by chance to have anti-Parkinsonian activity. Its mechanism of action in PD has not been established, but is believed to work by increasing dopamine release. Patients who receive amantidine either as monotherapy or in combination with levodopa show improvement in akinesia, rigidity and tremor.

Other medications used in the treatment of Parkinson's disease include MAO-B inhibitors. Inhibition of L-dopa metabolism through inactivation of the monoamino oxidase type B (MAO-B) is an effective means of enhancing the efficacy of both endogenous residual dopamine and that exogenously derived from its precursor, L-dopa. Selegiline (methyl-(1-methyl-2-phenyl-ethyl)-prop-2-ynyl-amine) is a MAO-B inhibitor. There is evidence that treatment with selegiline may slow down disease progression in PD by blocking formation of free radicals derived from the oxidative metabolism of dopamine. Other examples of MAO B inhibitors include lazabemide (N-(2-Aminoethyl)-5-chloro-2-pyridinecarboxamide), rasagiline (N-propargyl-1-(R)aminoindan and caroxazone (2-oxo-2H-1,3-benzoxazine-3(4H)-acetamide).

It is imperative to diagnose individuals with PD at an early stage and it is also important to determine the prognosis of the disease to increase the efficacy of therapeutic agents. However, there are neither any objective tests nor established biomarkers for diagnosing PD. Moreover, the heterogeneity, subtypes and progression of the disease make it difficult to develop specific therapeutic candidates.

MicroRNAs ("miRNAs) are a class of non-coding RNAs that play key roles in the regulation of gene expression. miRNAs act at the post-transcriptional level and fine-tune the expression of as much as 30% of all mammalian protein-encoding genes. Mature miRNAs are short, single-stranded RNA molecules approximately 22 nucleotides in length. miRNAs may be encoded by multiple loci, and may be organized in tandemly co-transcribed clusters. miRNA genes are transcribed by RNA polymerase II as large primary transcripts (pri-microRNA) that are processed by a protein complex containing the RNase III enzyme Drosha, DGCR8 and other cofactors, to form an approximately 70 nucleotide precursor microRNA (pre-miRNA). (Cathew R W, Cell, 2009; Kim V N, Nat Rev Mol Cel Biol, 2009; Siomi H, Mol Cel, 2010; Bartel D P, Cell, 2004; Lee Y, Nature 2003; Han J, Genes Dev, 2004.) Pre-miRNA is transported to the cytoplasm by Exportin-5 where it is processed by DICER, a second RNase III enzyme, together with TRBP, PACT and Ago2 in the RNA Induced Silencing Complex resulting in miRNA duplexes (Kim V N, Nat Rev Mol Cel Biol, 2009; Gregory R I, Nature 2004; MAcRae I J, PNAS, 2008). The guide strands of miRNA duplexes separate and associate with Ago 2 for incorporation into a ribonuclear particle to form the RNA-induced silencing complex RISC that mediates gene silencing. The mechanisms of miRNA range from direct degradation or silencing of mRNA and repression of translation to post-transcriptional upregulations. (MacRae I J, PNAS, 2008.)

The presence of miRNAs has been reported in body fluids including blood, cerebrospinal fluid (CSF), plasma, serum and saliva at detectable levels. The tissue-specificity of miRNAs suggests their vital and integral role in various physiological processes. The tissue-enrichment promises a new but less explored role as diagnostic biomarker and potential therapeutic target. Circulating miRNAs are understood to originate from passive leakage from damaged tissue as a result of cell lysis or apoptosis, active transport from cells via microvesicles, such as exosomes, or bound within RISC protein complexes (Etheridge et al, 2011). Exosome and osmotic pump-mediated delivery of small RNA molecules to the brain and CNS, respectively, provides a solution to overcoming the limitations of miRNA-based therapies (Alvarez-Erviti et al., 2011; Koval et al, 2013, Hum. Mol. Gen). miRNA has been demonstrated to be exceptionally stable and thus present as powerful candidates to be potential biomarkers (Chen et al, 2008; Grasso, 2014).

SUMMARY OF THE INVENTION

It is an object of the present invention to identify miRNAs relevant to patients suffering from Parkinson's disease.

It is another object of the present invention to provide methods for determining the rate of disease progression for patients suffering from Parkinson's disease.

It is another object of the present invention to determine the methods for determining treatment option based on the rate of progression of the disease for patients suffering from Parkinson's disease.

These objects and others are achieved by the present invention, which provides miRNA biomarkers that may be used singly, in pairs or in combination to determine patients suffering from Parkinson's disease.

DETAILED DESCRIPTION OF THE INVENTION

Figure 1:
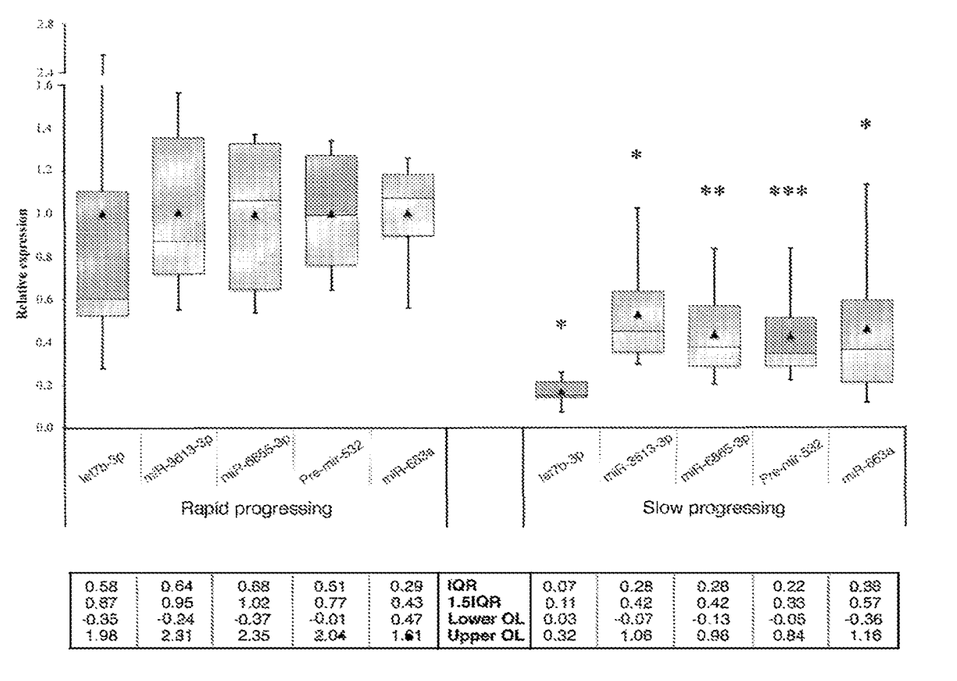
The FIGURE shows the mean fold change of five PrognomiRNAs between rapid and slow progressing PD patients.

Methods
Serum Samples Handling and Classification

All patients and controls participated in the Norwegian ParkWest project, which is an ongoing prospective population-based longitudinal cohort study investigating the incidence, neurobiology and prognosis of PD. The Norwegian ParkWest study is a prospective longitudinal multicenter cohort study of patients with incident Parkinson's disease (PD) from Western and Southern Norway. Between Nov. 1, 2004 and 31 of Aug. 2006 it was endeavored to recruit all new cases of Parkinson Disease within the study area. Since the start of the study 212 of 265 (80%) of these patients and their age-/sex-matched control group have been followed. Further information about the study can be found at www.parkvest.no.

All possible efforts were undertaken to establish an unselected and population-representative cohort of patients with PD. Patients were included if they had provided serum at study entry and fulfilled diagnostic criteria for PD of the National Institute of Neurological Disorders and Stroke www.ninds.nih.gov/disorders/parkinsons_disease/parkinsons_disease.htm) and UK Brain Bank (www.ncbi.nlm.nih.gov/projects/gap/cgi-bin/GetPdfcgi?id=phd000042) at latest follow-up. Patients with secondary parkinsonism at study entry were excluded from this study. Control subjects were recruited from multiple sources, including friends, spouses, and public organizations for elderly and were included in this study if they had provided serum. All patients and controls were Caucasian. The participants of the study have been followed for over eight years to establish the rate of disease progression.

In this study of possible biomarkers for PD we applied a two-stage procedure. For the first discovery phase serum from 8 patients with rapid and 8 patients with slow progression of PD were selected at random. The remaining 164 patients with PD that were eligible for this study were selected for verification purposes.

Serum samples were collected at the same day as the clinical examinations and then stored frozen at −70 degrees Celsius until transported to the facilities in New York on dry ice.

Example 1: Analyses of Differentially Expressed Human miRNA by qPCR RNA Isolation from Serum Samples and QC After thawing on ice, twenty-four (sixteen PD samples) serum samples were spun down for 5 mins at 3000xg to remove debris. The supernatant was used to perform small RNA isolation using miRCURY® RNA Isolation Kit—Biofluids (Exiqon, MA). Before RNA Isolation, the lysis buffer was spiked with 0.267 fmol/ul of spike-in control cel-miR-39-3p (Qiagen, CA). The remaining part of the RNA isolation was performed following manufacturer's protocol and the isolated RNA was quantified on a Nanodrop 2000 (Thermo Scientific, MA). The RNA was used for running Affymetrix v4 microRNA microarray chips and for subsequent cDNA synthesis and qPCR. RNA from 180 serum samples (from PD patients from ParkWest project) was isolated as described above, they were not quantified by Nanodrop, but the qPCR data resulting from these samples were normalized by a reference small RNA scaRNA17.

miRNA Microarray and Data Analysis

The isolated RNA from twenty-four patient serum samples were quantified and subjected to Affymetrix GeneChip® miRNA 4.0 Array by the Yale Center for Genome Analysis (www.medicine.yale.edu/keck/ycga/index.aspx). The normalized .CEL files obtained from Affymetrix Expression Console software were imported into Partek Genomics Suite version 6.6 Copyright © 2012 (Partek, MO) for analysis. The 'microRNA Expression Workflow' was employed to detect differentially expressed miRNAs employing ANOVA resulting in lists of miRNAs significantly ($p<0.05$) expressed between rapid and slow PD cohorts. The miRNAs detected were used for further qPCR verification.

Quantitative Polymerase Chain Reaction cDNA for miRNA specific qPCR was synthesized using qScript™ microRNA cDNA Synthesis kit (Quanta Biosciences, Md.) following manufacturer's protocol and subsequent qPCRs were performed using miRNA specific forward primers (Table #) and PerfeCTa® Universal PCR primer (Quanta Biosciences, Md.). scaRNA17 and U6 were used reference small RNAs for normalizing qPCR Cq values whereas cel-miR-39-3p was used as spike-in control. PerfeCTa® SYBR® GREEN SuperMix for IQ™ (Quanta Biosciences, Md.) was used for all qPCRs in a MyiQ™ Single color Real-Time PCR Detection System (Bio-Rad, Calif.). Standard curve for cel-miR-39-3p was analyzed in MS Excel with $R^2=0.97882$ and PCR efficiency 92.96%. No Template Control (NTC) was implied wherever needed.

Differentially expressed human miRNAs in Parkinson's disease patients' serum samples from The Norwegian Park-West study were determined employing miRNA microarray. Provided below are the miRNAs with >1.2 fold differential expression.

52 Differentially Expressed Human Pre- and Mature miRNAs with >1.2 Fold Change hsa-miR-6865-3p, hsa-miR-663a, hsa-miR-92b-3p, hsa-miR-455-3p, hsa-miR-93'7-5p, hsa-let-7b-3p, hsa-miR-6730-3p, hsa-miR-5010-3p, hsa-miR-1825, hsa-mir-4487, hsa-miR-4783-5p, hsa-miR-2117, hsa-mir-5090, hsa-mir-4484, hsa-miR-5094, hsa-mir-611, hsa-miR-4738-3p, hsa-miR-6894-5p, hsa-mir-8072, hsa-mir-762, hsa-let-7e, hsa-miR-6768-5p, hsa-mir-3917, hsa-mir-3673, hsa-mir-4431, hsa-miR-216a-3p, hsa-miR-635, hsa-miR-490-3p, hsa-mir-601, hsa-miR-636, hsa-miR-466, hsa-miR-1271-5p, hsa-miR-548u, hsa-miR-3606-5p, hsa-miR-510-5p, hsa-miR-4306, hsa-mir-4753, hsa-mir-6128, hsa-mir-4251, hsa-miR-1306-5p, hsa-miR-8052, hsa-mir-4310, hsa-mir-3128, hsa-miR-628-5p, hsa-miR-3660, hsa-miR-3156-3p, hsa-miR-548aj-3p, hsa-miR-4791, hsa-mir-532, hsa-miR-202-5p, hsa-miR-3613-3p, hsa-miR-8075

36 differentially expressed mature miRNAs with >1.2 fold change hsa-miR-6865-3p, hsa-miR-663a, hsa-miR-92b-3p, hsa-miR-455-3p, hsa-miR-937-5p, hsa-let-7b-3p, hsa-miR-6730-3p, hsa-miR-5010-3p, hsa-miR-1825, hsa-miR-4783-5p, hsa-miR-2117, hsa-miR-5094, hsa-miR-4738-3p, hsa-miR-6894-5p, hsa-let-7e, hsa-miR-6768-5p, hsa-miR-216a-3p, hsa-miR-635, hsa-miR-490-3p, hsa-miR-636, hsa-miR-466, hsa-miR-1271-5p, hsa-miR-548u, hsa-miR-3606-5p, hsa-miR-510-5p, hsa-miR-4306, hsa-miR-1306-5p, hsa-miR-8052, hsa-miR-628-5p, hsa-miR-3660, hsa-miR-3156-3p, hsa-miR-548aj-3p, hsa-miR-4791, hsa-miR-202-5p, hsa-miR-3613-3p, hsa-miR-8075

16 differentially expressed premature miRNAs with >1.2 fold change hsa-mir-4487, hsa-mir-5090, hsa-mir-4484, hsa-mir-611, hsa-mir-8072, hsa-mir-762, hsa-mir-3917, hsa-mir-3673, hsa-mir-4431, hsa-mir-601, hsa-mir-4753, hsa-mir-6128, hsa-mir-4251, hsa-mir-4310, hsa-mir-3128, hsa-mir-532, These differentially expressed miRNA sequences are illustrated below in Table 1, along with the reference/housekeeping small RNAs cel-miR-39-3p, U6 and ScaRNA17 used as controls. Cel-miR-39-3p is a spike-in control that demonstrates the stability of the RNA samples. U6 and ScaRNA17 are used as internal controls to normalize the readings of the rest of the miRNAs or candidate miRNAs.

Example 1

TABLE 1

| microRNA/ small RNA name | microRNA Sequence |
| --- | --- |
| hsa-let-7b-3p | CUAUACAACCUACUGCCUUCCC (SEQ ID NO:1) |
| hsa-let-7e | CCCGGGCUGAGGUAGGAGGUUGUAUAGUUG AGGAGGACACCCAAGGAGAAUCACUAUACGG CCUCCUAGCUUUCCCCAGG (SEQ ID NO:2) |
| hsa-miR-1271-5p | CUUGGCACCUAGCAAGCACUCA (SEQ ID NO:3) |
| hsa-miR-1306-5p | CCACCUCCCCUGCAAACGUCCA (SEQ ID NO:4) |
| hsa-miR-1825 | UCCAGUGCCCUCCUCUCC (SEQ ID NO:5) |
| hsa-miR-202-5p | UUCCUAUGCAUAUACUUCUUUG (SEQ ID NO:6) |

TABLE 1-continued

| microRNA/ small RNA name | microRNA Sequence |
| --- | --- |
| hsa-miR-2117 | UGUUCUCUUUGCCAAGGACAG (SEQ ID NO:7) |
| hsa-miR-216a-3p | UCACAGUGGUCUCUGGGAUUAU (SEQ ID NO:8) |
| hsa-mir-3128 | UUCCUCUGGCAAGUAAAAAACUCUCAUUUC CUUAAAAAAUGAGAGUUUUUUACUUGCAAU AGGAA (SEQ ID NO:9) |
| hsa-miR-3156-3p | CUCCCACUUCCAGAUCUUUCU (SEQ ID NO: 10) |
| hsa-miR-3606-5p | UUAGUGAAGGCUAUUUUAAUU (SEQ ID NO: 11) |
| hsa-miR-3613-3p | ACAAAAAAAAAAGCCCAACCCUUC (SEQ ID NO: 12) |
| hsa-miR-3660 | ACUGACAGGAGAGCAUUUUGA (SEQ ID NO: 13) |
| hsa-mir-3673 | AUAUAUAUAUAUGGAAUGUAUAUACGGAAUA UAUAUAUAUAUGGAAUGUAUAUACGGAAUAU AUAUAUAUAUGGAAUGUAUUACGGAAUAUAU AUAUAUAU (SEQ ID NO: 14) |
| hsa-mir-3917 | GGCGCUUUUGUGCGCGCCCGGGUCUGUUGGUG CUCAGAGUGUGGUCAGGCGGCUCGGACUGAGC AGGUGGGUGCGGGGCUCGGAGGAGGCGGC (SEQ ID NO: 15) |
| hsa-mir-4251 | CACGUCCUCCAGCUUUUUUCCUUAGUGGCCAA UUCCUGAGAAAAGGGCCAACGUGCUUCCA (SEQ ID NO: 16) |
| hsa-miR-4306 | UGGGAGAGAAAGGCAGUA (SEQ ID NO: 17) |
| hsa-mir-4310 | UGGCGUCUGGGGCCUGAGGCUGCAGAACAUUG CAGCAUUCAUGUCCCACCCCCACCA (SEQ ID NO: 18) |
| hsa-miR-4431 | UGGUUUGCGACUCUGAAAACUAGAAGGUUUA UGACUGGGCAUUUCUCACCCAAUGCCCAAUA UUGAACUUUCUAGUUGUCAGAGUCAUUAACCC (SEQ ID NO: 19) |
| hsa-mir-4484 | GGGUUUCCUCUGCCUUUUUUUCCAAUGAAAAU AACGAAACCUGUUAUUUCCCAUUGAGGGGGAA AAAGGCGGGAGAAGCCCCA (SEQ ID NO:20) |
| hsa-mir-4487 | ACUGUCCUUCAGCCAGAGCUGGCUGAAGGGCA GAAGGGAACUGUCCUUCAGCCAGAGCUGGCUG AAGGGCAGA (SEQ ID NO:21) |
| hsa-miR-455-3p | GCAGUCCAUGGGCAUAUACAC (SEQ ID NO:22) |
| hsa-miR-466 | AUACACAUACACGCAACACACAU (SEQ ID NO:23) |
| hsa-miR-4738-3p | UGAAACUGGAGCGCCUGGAGGA (SEQ ID NO:24) |
| hsa-mir-4753 | AUAUCUACACAAGGCCAAAGGAAGAGAACAGA UAUAUCCACAGUACACUUGGCUGUUCUCUUUC UUUAGCCUUGUGUAGAUAU (SEQ ID NO:25) |
| hsa-miR-4783-5p | GGCGCGCCCAGCUCCCGGGCU (SEQ ID NO:26) |
| hsa-miR-4791 | UGGAUAUGAUGACUGAAA (SEQ ID NO:27) |
| hsa-miR-490-3p | CAACCUGGAGGACUCCAUGCUG (SEQ ID NO:28) |
| hsa-miR-5010-3p | UUUUGUGUCUCCCAUUCCCCAG (SEQ ID NO:29) |
| hsa-mir-5090 | UCUGAGGUACCCGGGGCAGAUUGGUGUAGGGU GCAAAGCCUGCCGGCCCCCUAAGCCUUCUGCCC CCAACUCCAGCCUGUCAGGA (SEQ ID NO:30) |
| hsa-miR-5094 | AAUCAGUGAAUGCCUUGAACCU (SEQ ID NO:31) |
| hsa-miR-510-5p | UACUCAGGAGGGUGCAAUCAC (SEQ ID NO:32) |
| hsa-mir-532 | CGACUUGCUUUCUCUCCUCCAUGCCUUGAGUG UAGGACCGUUGGCAUCUUAAUUACCCUCCCAC ACCCAAGGCUUGCAGAAGAGCGAGCCU (SEQ ID NO:33) |
| hsa-miR-548aj-3p | UAAAAACUGCAAUUACUUUUA (SEQ ID NO:34) |
| hsa-miR-548u | CAAAGACUGCAAUUACUUUUGCG (SEQ ID NO:35) |
| hsa-mir-601 | UGCAUGAGUUCGUCUUGGUCUAGGAUUGUUG GAGGAGUCAGAAAAACUACCCCAGGGAUCCU GAAGUCCUUUGGGUGGA (SEQ ID NO:36) |
| hsa-mir-611 | AAAAUGGUGAGAGCGUUGAGGGGAGUUCCA GACGGAGAUGCGAGGACCCCUCGGGGUCUGA CCCACA (SEQ ID NO:37) |
| hsa-mir-6128 | AAGAAGCUUGUAGAUUUUUCUCCCUUACUAU CUAGAAUUAUAGGACUUCAGUCCAUGAUUUG GAAAAAUUACUGGAAUUGGAGUCAAAAAUA AUUUGAAAAUUAGGAAU (SEQ ID NO:38) |
| hsa-miR-628-5p | AUGCUGACAUAUUUACUAGAGG (SEQ ID NO:39) |
| hsa-miR-635 | ACUUGGGCACUGAAACAAUGUCC (SEQ ID NO:40) |
| hsa-miR-636 | UGUGCUUGCUCGUCCCGCCCGCA (SEQ ID NO:41) |
| hsa-miR-663a | AGGCGGGGCGCCGCGGGACCGC (SEQ ID NO:42) |
| hsa-miR-6730-3p | CCUGACACCCCAUCUGCCCUCA (SEQ ID NO:43) |

TABLE 1-continued

| microRNA/<br>small RNA name | microRNA Sequence |
|---|---|
| hsa-miR-6768-5p | CACACAGGAAAAGCGGGGCCCUG (SEQ ID NO:44) |
| hsa-miR-6865-3p | ACACCCUCUUUCCCUACCGCC (SEQ ID NO:45) |
| hsa-miR-6894-5p | AGGAGGAUGGAGAGCUGGGCCAGA (SEQ ID NO:46) |
| hsa-mir-762 | GGCCCGGCUCCGGGUCUCGGCCCGUACAGUCC GGCCGGCCAUGCUGGCGGGGCUGGGGCCGGG GCCGAGCCCGCGGCGGGGCC (SEQ ID NO:47) |
| hsa-miR-8052 | CGGGACUGUAGAGGGCAUGAGC (SEQ ID NO:48) |
| hsa-mir-8072 | GCGUCAAGAUGGCGGCGGGGAGGUAGGCAGA GCAGGACGCCGCUGCUGCCGCCGCCACCGCCG CCUCCGCUCCAGUCGCC (SEQ ID NO:49) |
| hsa-miR-8075 | UGCUGAUGGCAGAUGUCGGGUCUG (SEQ ID NO:50) |
| hsa-miR-92b-3p | UAUUGCACUCGUCCCGGCCUCC (SEQ ID NO:51) |
| hsa-miR-937-5p | GUGAGUCAGGGUGGGGCUGG (SEQ ID NO:52) |
| cel-miR-39-3p | UCACCGGGUGUAAAUCAGCUUG (SEQ ID NO:53) |
| scaRNA17 | AGAGGCUUGGGCCGCCGAGCUGGACCCGGAC CGGUUUUGGGUACUGUACUGGGGGCAGGGCA GAGAGGG (SEQ ID NO:54) |
| U6 | GUGCUCGCUUCGGCAGCACAUAUACUAAAAUU GGAACGAUACAGAGAAGAUUAGCAUGGCCCCU GCGCAAGGAUGACACGCAAAUUCGUGAAGCGU UCCAUAUUUU (SEQ ID NO:55) |

Example 2: Verification of Human Mature miRNAs by qPCR in Sample Cohort of Eight Rapid and Eight Slow Progressing Patients The mean fold change for hsa-let7b-3p, hsa-miR-3613-3p and hsa-miR-6865-3p, hsa-pre-miR-532, and hsa-miR-663a, PrognomiRs between rapid and slow progressing PD patients are shown below in Table 2 and illustrated in the FIGURE.

TABLE 2

| PrognomiR | Fold change | Significance |
|---|---|---|
| hsa-let7b-3p | 0.17 | 0.02 |
| hsa-miR-3613-3p | 0.53 | 0.01 |
| hsa-miR-6865-3p | 0.44 | 0.002 |
| hsa-pre-miR-532 | 0.43 | 0.0005 |
| hsa-miR-663a | 0.46 | 0.01 |

The median values for relative expression of let7b-3p, miR-3613-3p, miR-6865-3p, pre-mir-532 and miR-663a are plotted as lines with each box displaying inner quartiles as a measure of distribution with whiskers. Results shown are derived qTR-PCR verification performed in initial eight rapid and eight slow progressing PD patients. Means for each group are denoted as triangles on the plot. Significance is denoted as *, p<0.05; , p<0.01; *, p<0.001.

Example 3

Measurement of levels of a combination of two or more miRNAs in serum from patients can assist in distinctly differentiating between a potential rapid as opposed to slow progressing PD patient. A serum sample is obtained from blood withdrawn from patients suspected of PD. The serum is used for total microRNA isolation and enrichment. This RNA would then be tested using qPCR to measure the levels of any two or more of the 52 miRNAs mentioned in Example 1, or any one of five miRNAs mentioned in Example 2. Detectable levels of one or more of the aforementioned 52 miRNAs with >1.2 fold change, or any one or more of these five miRNAs confirms the rate of progression for patients with PD. If desired, other sample fluids may be utilized, including plasma, venous or arterial blood, or CSF samples withdrawn by lumbar puncture. Such plasma, blood or CSF samples are processed as discussed above regarding serum, e.g., so as to provide a sample for processing and evaluation outside the human or animal body. It will be understood that measurement of more than two miRNAs in combination or a set of combinations used in a test matrix may desirably increase the accuracy of predicting PD progression. Following diagnosis, the result is then communicated to the patient.

As discussed and illustrated above, detecting the aforementioned miRNAs with >1.2 fold change may be used to differentiate potential rapid progressing PD from potential slow progressing PD in afflicted patients. However, as readily understood by those of ordinary skill herein, other thresholds may be suitably employed as desired with possible concomitant variation in accuracy, including >1.0, 1.1, 1.3, 1.4, 1.5, 1.6, 1.7, 1.8, 1.9, and 2.0 fold changes. Moreover, it will be similarly understood that these varying fold change thresholds may be more suitably used with particular miRNAs without affecting accuracy.

Example 4

Since a combination of miRNA can be used for predicting prognosis it may be advisable to test all the candidates to eliminate any cohort-based variation. It is understood that any detectable amounts of relevant miRNA will indicate PD pathology. However, those of ordinary skill in the art recognize it may be clinically helpful to use values of slow (8) v rapid (8) samples to set an artificial threshold for determination of rate of disease progression. Differential miRNA levels can be used to develop prognostic biomarker kits that can be used by clinicians for estimating prognosis of the disease as well as enriching patient cohorts in clinical trials. In this study the presence and quantification of miRNA from serum was determined by qRT-PCR which amplifies and quantifies the RNA is question. Other suitable techniques known to those of ordinary skill herein may be alternatively utilized, including use of labeled antisense sequences and labeled antibodies. Suitable antibodies are preferentially selective, referring to a binding reaction between two molecules that is typically more than 10 to 100 times background molecular associations under measurement conditions. Thus, under designated immunoassay conditions, the specified antibodies bind to a particular miRNA sequence, thereby identifying its presence. Specific binding to an antibody under such conditions requires an antibody that is selected for its specificity for a particular miRNA. For example, antibodies raised against a particular miRNA can be selected by subtracting out antibodies that cross-react with other molecules. A variety of immunoassay formats may be used to select antibodies specifically immunoreactive with a particular miRNA including solid-phase ELISA immunoassays (see, e.g., Harlow & Lane, Antibodies, A Laboratory Manual (1988) for a description of immunoassay formats and conditions that can be used to determine specific immunoreactivity). Methods for determining whether two molecules specifically interact are disclosed therein, and methods of determining binding affinity and specificity are well known in the art (see, for example, Harlow and Lane, Antibodies: A laboratory manual (Cold Spring Harbor Laboratory Press, 1988); Friefelder, "Physical Biochemistry: Applications to biochemistry and molecular biology" (W.H. Freeman and Co. 1976)). The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')2, Fab, Fv and rIgG). See also, Pierce Catalog and Handbook, 1994-1995 (Pierce Chemical Co., Rockford, Ill.). See also, e.g., Kuby, J., Immunology, 3rd Ed., W.H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science, Vol. 246 (1989) 1275-81. These and other methods of making, for example, chimeric, humanized, CDR-grafted, single chain, and bifunctional antibodies are well known to those skilled in the art (Winter and Harris, Immunol. Today, Vol. 14 (1993) 243-46; Ward et al., Nature, Vol. 341 (1989) 544-46; Harlow and Lane, supra, 1988; Hilyard et al., Protein Engineering: A practical approach (IRL Press 1992); Borrabeck, Antibody Engineering, 2d ed. (Oxford University Press 1995). Methods for producing both monoclonal and polyclonal antibodies from identified RNA sequences are well known in the art.

Example 5

Many neurodegenerative diseases are closely related to each other when it comes to symptoms as well as pathological markers. The circulating prognostic markers for one neurodegenerative disease can be useful for diagnosis/prognosis of other disease. A method to diagnose/prognoses other neurodegenerative diseases like Dementia with Lewy body (DLB), Amyotrophic lateral sclerosis (ALS), Alzheimer's disease (AD), Multiple system atrophy (MSA), CortiocoBasal Degeneration (CBD), Progressive Supranuclear Palsy (PSP) can also be developed using similar miRNA measurements of candidates mentioned above. Disease specific kits can be developed similar to one mentioned in [0024] with various combinations of miRNAs listed in [0018].

Example 6

The miRNAs detected in one or more combinations can regulate several proteins in the cells. Novel protein targets for PD can be discovered using these microRNAs and their combinations. The involvement of these proteins in PD etiology can be further established to target them for therapy.

Example 7

Small nucleic acid molecules derived from miRNAs mentioned in [0018] will be designed to therapeutically intervene by specifically targeting genes in PD brains to achieve complete or partial remedy.

---

What is claimed is:

1. A method for treating a human patient with rapid progressing Parkinson's disease, comprising the steps of, in this order:

obtaining a first sample comprising serum, plasma or blood from said patient;

determining a level of expression of at least one miRNA selected from the group consisting of SEQ ID NOS: 1, 12, 42 and 45, and optionally further determining a level of expression of at least one miRNA selected from the group consisting of SEQ ID NOS: 2, 3, 4, 5, 6, 7, 8, 9, 10, 11, 13, 14, 15, 16, 17, 18, 19, 20, 21, 22, 23, 24, 25, 26, 27, 28, 29, 30, 31, 32, 33, 34, 35, 36, 37, 38, 39, 40, 41, 43, 44, 46, 47, 48, 49, 50, 51 and 52 within said first sample;

comparing the level of expression of the determined SEQ ID NOS to a level of expression of the determined SEQ ID NOS in a second sample from a cohort with slow progressing Parkinson's disease and confirming the expression level of the determined SEQ ID NOS in said first sample is greater than 1.2-fold over that of said second sample, thereby indicating the patient has rapid progressing Parkinson's disease; and treating said rapid progressing Parkinson's disease with at least one of L-dopa, a dopamine agonist, a catechol-O-methyltransferase (COMT) inhibitor, amantidine (1-Aminotricyclo $(3,3,1,1^{3,7})$ decane or a monoamino oxidase type B inhibitor.

2. The method according to claim 1, wherein expression of miRNAs according to at least two of said SEQ ID NOS: 1, 12, 42 and 45 is compared relative to the cohort.

3. The method according to claim 2, wherein expression of miRNAs according to at least SEQ ID NOS: 1 and 12 is compared relative to the cohort.

4. The method according to claim 2, wherein expression of miRNAs according to at least SEQ ID NOS: 1 and 42 is compared relative to the cohort.

5. The method according to claim 2, wherein expression of miRNAs according to at least SEQ ID NOS: 1 and 45 is compared relative to the cohort.

6. The method according to claim 2, wherein expression of miRNAs according to at least SEQ ID NOS: 12 and 42 is compared relative to the cohort.

7. The method according to claim 2, wherein expression of miRNAs according to at least SEQ ID NOS: 12 and 45 is compared relative to the cohort.

8. The method according to claim 2, wherein expression of miRNAs according to at least SEQ ID NOS: 42 and 45 is compared relative to the cohort.

9. The method according to claim 2, wherein expression of miRNAs according to SEQ ID NO: 33 is also compared relative to the cohort.

10. The method according to claim 2, wherein expression of miRNAs according to at least three of said SEQ ID NOS: 1, 12, 42 and 45 is compared relative to the cohort.

11. The method according to claim 10, wherein expression of miRNAs according to at least SEQ ID NOS: 1, 12 and 42 is compared relative to the cohort.

12. The method according to claim 10, wherein expression of miRNAs according to at least SEQ ID NOS: 1, 12 and 45 is compared relative to the cohort.

13. The method according to claim 10, wherein expression of miRNAs according to at least SEQ ID NOS: 1, 42 and 45 is compared relative to the cohort.

14. The method according to claim 10, wherein expression of miRNAs according to at least SEQ ID NOS: 12, 42 and 45 is compared relative to the cohort.

15. The method according to claim 10, wherein expression of miRNAs according to SEQ ID NO: 33 is also compared relative to the cohort.

16. The method according to claim 10, wherein expression of miRNAs according to each of said SEQ ID NOS: 1, 12, 42 and 45 is compared relative to the cohort.

17. The method according to claim 16, wherein expression of miRNAs according to SEQ ID NO: 33 is also compared relative to the cohort.

18. The method according to claim 1, wherein expression of miRNAs according to SEQ ID NO: 33 is also compared relative to the cohort.

19. The method according to claim 1, wherein said first sample comprises serum.

* * * * *

SEQUENCE LISTING

```
<160> NUMBER OF SEQ ID NOS: 55

<210> SEQ ID NO 1
<211> LENGTH: 22
<212> TYPE: RNA
<213> ORGANISM: Homo sapiens

<400> SEQUENCE: 1
cuauacaacc uacugccuuc cc                                                  22

<210> SEQ ID NO 2
<211> LENGTH: 79
<212> TYPE: RNA
<213> ORGANISM: Homo sapiens

<400> SEQUENCE: 2
cccgggcuga gguaggaggu uguauaguug aggaggacac ccaaggagau cacuauacgg         60
ccuccuagcu uuccccagg                                                      79

<210> SEQ ID NO 3
<211> LENGTH: 22
<212> TYPE: RNA
<213> ORGANISM: Homo sapiens

<400> SEQUENCE: 3
cuuggcaccu agcaagcacu ca                                                  22

<210> SEQ ID NO 4
<211> LENGTH: 22
<212> TYPE: RNA
<213> ORGANISM: Homo sapiens

<400> SEQUENCE: 4
ccaccucccc ugcaaacguc ca                                                  22
```

```
<210> SEQ ID NO 5
<211> LENGTH: 18
<212> TYPE: RNA
<213> ORGANISM: Homo sapiens

<400> SEQUENCE: 5
uccagugccc uccucucc                                                       18

<210> SEQ ID NO 6
<211> LENGTH: 22
<212> TYPE: RNA
<213> ORGANISM: Homo sapiens

<400> SEQUENCE: 6
uuccuaugca uauacuucuu ug                                                  22

<210> SEQ ID NO 7
<211> LENGTH: 21
<212> TYPE: RNA
<213> ORGANISM: Homo sapiens

<400> SEQUENCE: 7
uguucucuuu gccaaggaca g                                                   21

<210> SEQ ID NO 8
<211> LENGTH: 22
<212> TYPE: RNA
<213> ORGANISM: Homo sapiens

<400> SEQUENCE: 8
ucacaguggu cucugggauu au                                                  22

<210> SEQ ID NO 9
<211> LENGTH: 66
<212> TYPE: RNA
<213> ORGANISM: Homo sapiens

<400> SEQUENCE: 9
uuccucuggc aaguaaaaaa cucucauuuu ccuuaaaaaa ugagaguuuu uuacuugcaa         60
uaggaa                                                                   66

<210> SEQ ID NO 10
<211> LENGTH: 21
<212> TYPE: RNA
<213> ORGANISM: Homo sapiens

<400> SEQUENCE: 10
cucccacuuc cagaucuuuc u                                                   21

<210> SEQ ID NO 11
<211> LENGTH: 21
<212> TYPE: RNA
<213> ORGANISM: Homo sapiens

<400> SEQUENCE: 11
uuagugaagg cuauuuuaau u                                                   21

<210> SEQ ID NO 12
<211> LENGTH: 24
<212> TYPE: RNA
<213> ORGANISM: Homo sapiens
```

```
<400> SEQUENCE: 12
acaaaaaaaa aagcccaacc cuuc                                          24

<210> SEQ ID NO 13
<211> LENGTH: 21
<212> TYPE: RNA
<213> ORGANISM: Homo sapiens

<400> SEQUENCE: 13
acugacagga gagcauuuug a                                             21

<210> SEQ ID NO 14
<211> LENGTH: 101
<212> TYPE: RNA
<213> ORGANISM: Homo sapiens

<400> SEQUENCE: 14
auauauauau auggaaugua uaucggaau auauauauau auggaaugua uaucggaau     60 auauauauau auggaaugua uuacggaaua uauauauaua u                      101

<210> SEQ ID NO 15
<211> LENGTH: 93
<212> TYPE: RNA
<213> ORGANISM: Homo sapiens

<400> SEQUENCE: 15
ggcgcuuuug ugcgcgcccg ggucuguugg ugcucagagu guggucaggc ggcucggacu   60
gagcaggugg gugcggggcu cggaggaggc ggc                                93

<210> SEQ ID NO 16
<211> LENGTH: 61
<212> TYPE: RNA
<213> ORGANISM: Homo sapiens

<400> SEQUENCE: 16
cacguccucc agcuuuuuuc cuuaguggcc aauuccugag aaaagggcca acgugcuucc   60
a                                                                   61

<210> SEQ ID NO 17
<211> LENGTH: 17
<212> TYPE: RNA
<213> ORGANISM: Homo sapiens

<400> SEQUENCE: 17
uggagagaaa ggcagua                                                  17

<210> SEQ ID NO 18
<211> LENGTH: 57
<212> TYPE: RNA
<213> ORGANISM: Homo sapiens

<400> SEQUENCE: 18
uggcgucugg ggccugaggc ugcagaacau ugcagcauuc augucccacc cccacca      57

<210> SEQ ID NO 19
<211> LENGTH: 94
<212> TYPE: RNA
<213> ORGANISM: Homo sapiens

<400> SEQUENCE: 19
ugguuugcga cucugaaaac uagaagguuu augacugggc auuucucacc caaugcccaa   60
```
uauugaacuu ucuaguuguc agagucauua accc    94

<210> SEQ ID NO 20
<211> LENGTH: 83
<212> TYPE: RNA
<213> ORGANISM: Homo sapiens

<400> SEQUENCE: 20 ggguuccuc ugccuuuuuu uccaaugaaa auaacgaaac cuguuauuuc ccauugaggg    60
ggaaaaaggc gggagaagcc cca    83

<210> SEQ ID NO 21
<211> LENGTH: 73
<212> TYPE: RNA
<213> ORGANISM: Homo sapiens

<400> SEQUENCE: 21
acuguccuuc agccagagcu ggcugaaggg cagaagggaa cuguccuuca gccagagcug    60
gcugaagggc aga    73

<210> SEQ ID NO 22
<211> LENGTH: 21
<212> TYPE: RNA
<213> ORGANISM: Homo sapiens

<400> SEQUENCE: 22
gcaguccaug ggcauauaca c    21

<210> SEQ ID NO 23
<211> LENGTH: 23
<212> TYPE: RNA
<213> ORGANISM: Homo sapiens

<400> SEQUENCE: 23
auacacauac acgcaacaca cau    23

<210> SEQ ID NO 24
<211> LENGTH: 22
<212> TYPE: RNA
<213> ORGANISM: Homo sapiens

<400> SEQUENCE: 24
ugaaacugga gcgccuggag ga    22

<210> SEQ ID NO 25
<211> LENGTH: 83
<212> TYPE: RNA
<213> ORGANISM: Homo sapiens

<400> SEQUENCE: 25
auaucuacac aaggccaaag gaagagaaca gauauaucca caguacacuu ggcuguucuc    60
uuucuuuagc cuuguguaga uau    83

<210> SEQ ID NO 26
<211> LENGTH: 21
<212> TYPE: RNA
<213> ORGANISM: Homo sapiens

<400> SEQUENCE: 26
ggcgcgccca gcucccgggc u    21

```
<210> SEQ ID NO 27
<211> LENGTH: 18
<212> TYPE: RNA
<213> ORGANISM: Homo sapiens

<400> SEQUENCE: 27
uggauaugau gacugaaa                                                    18

<210> SEQ ID NO 28
<211> LENGTH: 22
<212> TYPE: RNA
<213> ORGANISM: Homo sapiens

<400> SEQUENCE: 28
caaccuggag gacuccaugc ug                                               22

<210> SEQ ID NO 29
<211> LENGTH: 22
<212> TYPE: RNA
<213> ORGANISM: Homo sapiens

<400> SEQUENCE: 29
uuuugugucu cccauucccc ag                                               22

<210> SEQ ID NO 30
<211> LENGTH: 85
<212> TYPE: RNA
<213> ORGANISM: Homo sapiens

<400> SEQUENCE: 30
ucugagguac ccggggcaga uugguguagg gugcaaagcc ugcccgcccc cuaagccuuc      60
ugcccccaac uccagccugu cagga                                            85

<210> SEQ ID NO 31
<211> LENGTH: 22
<212> TYPE: RNA
<213> ORGANISM: Homo sapiens

<400> SEQUENCE: 31
aaucagugaa ugccuugaac cu                                               22

<210> SEQ ID NO 32
<211> LENGTH: 22
<212> TYPE: RNA
<213> ORGANISM: Homo sapiens

<400> SEQUENCE: 32
uacucaggag aguggcaauc ac                                               22

<210> SEQ ID NO 33
<211> LENGTH: 91
<212> TYPE: RNA
<213> ORGANISM: Homo sapiens

<400> SEQUENCE: 33
cgacuugcuu ucucuccucc augccuugag uguaggaccg uuggcaucuu aauuacccuc      60
ccacacccaa ggcuugcaga agagcgagcc u                                     91

<210> SEQ ID NO 34
<211> LENGTH: 21
<212> TYPE: RNA
<213> ORGANISM: Homo sapiens
```

```
<400> SEQUENCE: 34
uaaaaacugc aauuacuuuu a                                              21

<210> SEQ ID NO 35
<211> LENGTH: 23
<212> TYPE: RNA
<213> ORGANISM: Homo sapiens

<400> SEQUENCE: 35
caaagacugc aauuacuuuu gcg                                            23

<210> SEQ ID NO 36
<211> LENGTH: 79
<212> TYPE: RNA
<213> ORGANISM: Homo sapiens

<400> SEQUENCE: 36
ugcaugaguu cgucuugguc uaggauuguu ggaggaguca gaaaaacuac cccagggauc    60
cugaagyccu uugggugga                                                 79

<210> SEQ ID NO 37
<211> LENGTH: 67
<212> TYPE: RNA
<213> ORGANISM: Homo sapiens

<400> SEQUENCE: 37
aaaaugguga gagcguugag gggaguucca gacggagaug cgaggacccc ucgggqucug    60 acccaca                                                              67

<210> SEQ ID NO 38
<211> LENGTH: 109
<212> TYPE: RNA
<213> ORGANISM: Homo sapiens

<400> SEQUENCE: 38
aagaagcuug uagauuuuuc ucccuuacua ucuagaauua uaggacuuca guccaugauu    60
uggaaaaauu acuggaauug gagucaaaaa uaauuugaaa auuaggaau              109

<210> SEQ ID NO 39
<211> LENGTH: 22
<212> TYPE: RNA
<213> ORGANISM: Homo sapiens

<400> SEQUENCE: 39
augcugacau auuuacuaga gg                                             22

<210> SEQ ID NO 40
<211> LENGTH: 23
<212> TYPE: RNA
<213> ORGANISM: Homo sapiens

<400> SEQUENCE: 40
acuugggcac ugaaacaaug ucc                                            23

<210> SEQ ID NO 41
<211> LENGTH: 23
<212> TYPE: RNA
<213> ORGANISM: Homo sapiens

<400> SEQUENCE: 41
```
ugugcuugcu cgucccgccc gca                                            23

<210> SEQ ID NO 42
<211> LENGTH: 22
<212> TYPE: RNA
<213> ORGANISM: Homo sapiens

<400> SEQUENCE: 42
aggcggggcg ccgcgggacc gc                                             22

<210> SEQ ID NO 43
<211> LENGTH: 22
<212> TYPE: RNA
<213> ORGANISM: Homo sapiens

<400> SEQUENCE: 43
ccugacaccc caucugcccu ca                                             22

<210> SEQ ID NO 44
<211> LENGTH: 23
<212> TYPE: RNA
<213> ORGANISM: Homo sapiens

<400> SEQUENCE: 44
cacacaggaa aagcggggcc cug                                            23

<210> SEQ ID NO 45
<211> LENGTH: 21
<212> TYPE: RNA
<213> ORGANISM: Homo sapiens

<400> SEQUENCE: 45
acacccucuu ucccuaccgc c                                              21

<210> SEQ ID NO 46
<211> LENGTH: 24
<212> TYPE: RNA
<213> ORGANISM: Homo sapiens

<400> SEQUENCE: 46
aggaggaugg agagcugggc caga                                           24

<210> SEQ ID NO 47
<211> LENGTH: 83
<212> TYPE: RNA
<213> ORGANISM: Homo sapiens

<400> SEQUENCE: 47
ggcccggcuc cgggucucgg cccguacagu ccggccggcc augcuggcgg ggcuggggcc    60
ggggccgagc ccgcggcggg gcc                                            83

<210> SEQ ID NO 48
<211> LENGTH: 22
<212> TYPE: RNA
<213> ORGANISM: Homo sapiens

<400> SEQUENCE: 48
cgggacugua gagggcauga gc                                             22

<210> SEQ ID NO 49
<211> LENGTH: 80
<212> TYPE: RNA
<213> ORGANISM: Homo sapiens

```
<400> SEQUENCE: 49
gcgucaagau ggcggcgggg agguaggcag agcaggacgc cgcugcugcc gccgccaccg    60
ccgccuccgc uccagucgcc                                                80

<210> SEQ ID NO 50
<211> LENGTH: 24
<212> TYPE: RNA
<213> ORGANISM: Homo sapiens

<400> SEQUENCE: 50
ugcugauggc agaugucggg ucug                                           24

<210> SEQ ID NO 51
<211> LENGTH: 22
<212> TYPE: RNA
<213> ORGANISM: Homo sapiens

<400> SEQUENCE: 51
uauugcacuc gucccggccu cc                                             22

<210> SEQ ID NO 52
<211> LENGTH: 20
<212> TYPE: RNA
<213> ORGANISM: Homo sapiens

<400> SEQUENCE: 52
gugagucagg gugggcugg                                                 20

<210> SEQ ID NO 53
<211> LENGTH: 22
<212> TYPE: RNA
<213> ORGANISM: Caenorhabditis elegans

<400> SEQUENCE: 53
ucaccgggug uaaaucagcu ug                                             22

<210> SEQ ID NO 54
<211> LENGTH: 69
<212> TYPE: RNA
<213> ORGANISM: Homo sapiens

<400> SEQUENCE: 54
agaggcuugg gccgccgagc uggacccgga ccgguuuugg guacuguacu gggggcaggg    60
cagagaggg                                                            69

<210> SEQ ID NO 55
<211> LENGTH: 106
<212> TYPE: RNA
<213> ORGANISM: Homo sapiens

<400> SEQUENCE: 55
gugcucgcuu cggcagcaca uauacuaaaa uuggaacgau acagagaaga uuagcauggc    60
cccugcgcaa ggaugacacg caaauucgug aagcguucca uauuuu                  106
```

UNITED STATES PATENT AND TRADEMARK OFFICE
CERTIFICATE OF CORRECTION

| | |
|---|---|
| PATENT NO. | : 11,739,384 B2 |
| APPLICATION NO. | : 16/623870 |
| DATED | : August 29, 2023 |
| INVENTOR(S) | : Simon Geir Moller et al. |

It is certified that error appears in the above-identified patent and that said Letters Patent is hereby corrected as shown below:

On the Title Page

<u>IN THE ABSTRACT</u>
Item (57), "patient's suffering from" should read --patients suffering with--

In the Specification

<u>Column 1</u>
Line 23, "Parkinson's Disease" should read --Parkinson's disease--
Lines 26, "people world-wide." should read --people worldwide.--
Lines 28-29, "often debilitating" should read --often-debilitating--
Line 30, "Fluctuations (LMF) occur." should read --Fluctuations (LMF), occurs.--
Lines 45-46, "controlled release" should read --controlled-release--
Line 47, "controlled release" should read --controlled-release--
Line 47, "(2-Amino-3" should read --(2-amino-3--
Line 59, "((5a)-2-Bromo-" should read --((5α-2-Bromo--
Lines 60-61, "erg-otaman" should read --ergotaman--

<u>Column 2</u>
Line 1, "7-Tetrahydro-6" should read --7-tetrahydro-6--
Line 6, "5,6,7,8-Tetrahydro" should read --5,6,7,8-tetrahydro--
Line 45, "MicroRNAs ("miRNAs)" should read --MicroRNAs ("miRNAs"--
Lines 56-57, "70 nucleotide precursor" should read --70-nucleotide precursor--
Lines 60-61, "transported to the cytoplasm by Exportin-5 where it" should read --transported by Exportin-5 to the cytoplasm, where it--
Lines 63-64, "in the RNA Induced Silencing Complex resulting" should read --in the RNA-induced silencing complex, resulting--
Line 65, "MAcRae I J," should read --MacRae I J,--
Line 67, "with Ago 2 for" should read --with Ago2 for--

Signed and Sealed this
Seventeenth Day of October, 2023

Katherine Kelly Vidal
*Director of the United States Patent and Trademark Office*

CERTIFICATE OF CORRECTION (continued)
U.S. Pat. No. 11,739,384 B2

Column 3
Line 1, "complex RISC" should read --complex (RISC)--
Line 16, "Etheridge et al," should read --Etheridge et al.,--
Line 20, "Koval et al," should read --Koval et al.,--
Line 22, "and thus present as" should read --and thus presents as--
Line 23, "(Chen et al," should read --(Chen et al.,--
Line 33, "treatment option" should read --treatment options--
Line 58, "and 31 of Aug. 2006 it was endeavored" should read --and Aug. 31, 2006, the study endeavored--
Line 59, "of Parkinson Disease" should read --of Parkinson's disease--
Lines 62-63, "www-.parkvest.no." should read --www.parkvest.no.--

Column 4
Line 2, "www.ninds.nih" should read --(www.ninds.nih--
Lines 3-4, "nlm.nih-.gov" should read --nlm.nih.gov--
Line 8, "for elderly and" should read --for the elderly and--
Line 17, "PD that were" should read --PD who were--
Line 32, "RNA Isolation," should read --RNA isolation,--
Line 41, "above, they were" should read --above. They were--
Line 46, "samples were quantified" should read --samples was quantified--
Lines 51-52, "The 'microRNA Expression Workflow' was" should read --The "microRNA Expression Workflow" was--
Line 54, "ANOVA resulting" should read --ANOVA, resulting--
Line 62, "miRNA specific" should read --miRNA-specific--
Line 63, "(Table #)," should read --Table 1--
Lines 64-65, "were used reference" should read --were used as reference--

Column 5
Lines 28-29, "36 differentially expressed mature miRNAs with >1.2 fold change" should read --36 Differentially Expressed Mature miRNAs with >1.2 Fold Change--
Lines 40-41, "16 differentially expressed premature miRNAs with >1.2 fold change" should read --16 Differentially Expressed Premature miRNAs with >1.2 Fold Change--
Lines 44-45, "hsa-mir-532, These" should read --hsa-mir-532. These--

Column 7
Lines 31-33, "hsa-miR-3613-3p and hsa-miR-6865-3p, hsa-pre-miR-532, and hsa-miR-663a, PrognomiRs" should read --hsa-miR-3613-3p, hsa-miR-6865-3p, hsa-pre-miR-532, and hsa-miR-663a PrognomiRs--
Line 34, "patients are shown" should read --patients is shown--

Column 8
Line 1, "miRNAs confirms the" should read --miRNAs confirm the--
Lines 32-33, "slow (8) v rapid" should read --slow (8) vs. rapid--
Line 39, "serum was determined" should read --serum were determined--
Lines 39-40, "qRT-PCR which amplifies and quantifies the RNA is question." should read --qRT-PCR, which amplifies and quantifies the RNA in question--

CERTIFICATE OF CORRECTION (continued)
U.S. Pat. No. 11,739,384 B2

Line 56, "miRNA including" should read --miRNA, including--
Line 67, "and Co. 1976))." should read --and Co., 1976)).--

Column 9
Line 5, "thereof, (e.g.," should read --thereof (e.g.,--
Line 8, "3rd Ed.," should read --3rd ed.,--
Line 10, "solid phase peptide" should read --solid-phase peptide--
Line 21, "Press 1995)." should read --Press 1995)).--

Column 10
Line 3, "method to diagnose/prognoses" should read --method to provide a diagnosis or prognosis--
Lines 4-5, "Dementia with Lewy body (DLB), Amyotrophic lateral" should read --dementia with Lewy body (DLB), amyotrophic lateral--
Lines 6-8, "Multiple system atrophy (MSA), CorticoBasal Degeneration (CBD), Progressive Supranuclear Palsy" should read --multiple system atrophy (MSA), corticobasal degeneration (CBD), and progressive supranuclear palsy--
Lines 9-10, "Disease specific kits" should read --Disease-specific kits--